US00PP16185P3

(12) United States Plant Patent
Jorgensen

(10) Patent No.: US PP16,185 P3
(45) Date of Patent: Jan. 3, 2006

(54) STAGHORN SUMAC PLANT NAMED 'BAILTIGER'

(50) Latin Name: *Rhus typhina*
Varietal Denomination: Bailtiger

(75) Inventor: Steven Jorgensen, Hastings, MN (US)

(73) Assignee: Bailey Nurseries, Inc., St. Paul, MN (US)

( * ) Notice: Subject to any disclaimer, the term of this patent is extended or adjusted under 35 U.S.C. 154(b) by 145 days.

(21) Appl. No.: 10/835,573

(22) Filed: Apr. 30, 2004

(65) Prior Publication Data

US 2005/0246805 P1 Nov. 3, 2005

(51) Int. Cl.
*A01H 5/00* (2006.01)

(52) U.S. Cl. ..... Plt./216

(58) Field of Classification Search ..... Plt./216
See application file for complete search history.

*Primary Examiner*—Anne Marie Grunberg
*Assistant Examiner*—Annette H Para
(74) *Attorney, Agent, or Firm*—Burns, Doane, Swecker & Mathis, LLP

(57) ABSTRACT

A new and distinct highly ornamental cultivar of *Rhus typhina* is provided. This Staghorn Sumac plant displays a dwarf, compact and spreading growth habit with a somewhat flat crown. Attractive chartreuse green foliage initially is formed that quickly largely changes to bright yellow. Predominantly yellow foliage is displayed in the fall together with some scarlet coloration. During observations to date the plant has been relatively free of insect and disease problems. The plant is well-suited for providing distinctive colorful ornamentation in the landscape.

3 Drawing Sheets

Botanical commercial classification: *Rhus typhina*/Staghorn Sumac Shrub.
Varietal denomination: cv. 'Bailtiger'.

SUMMARY OF THE INVENTION

The new Staghorn Sumac shrub of the present invention was discovered during July 1985 while growing in a block of *Rhus typhina* 'Laciniata' plants (non-patented in the United States) in a cultivated nursery setting at St. Paul, Minn., U.S.A. The distinctive bright yellow foliage and the diminutive growth habit of the plant were considered to be significant and the plant was preserved for further testing and evaluation. This observed distinctive combination of characteristics was determined not to be the result of abnormal soil conditions. The new cultivar is believed to be a whole plant mutation of unknown causation of the 'Laciniata' cultivar. Had this single plant of the new cultivar not been discovered and preserved it would have been lost to mankind.

It was found that this new *Rhus typhina* cultivar exhibits the following combination of characteristics:

(a) exhibits a dwarf growth habit, (b) forms attractive chartreuse green new foliage that quickly largely changes to bright yellow, and in the fall displays predominantly yellow foliage with some scarlet coloration, (c) is relatively free of insect and disease problems, and (d) is well-suited for growing as a distinctive ornamental shrub in the landscape.

The new cultivar of the present invention provides a pleasing and colorful display or ornamentation. The vegetation is vigorous, bold and architectural. The plant can be grown to advantage as a specimen shrub or as a mass planting. It also can be used to provide coloration behind a shrub or perennial border planting. The plant performs best in sunny setting and once established is relatively drought tolerant. The plant has been found to be relative hardy and to suitable for growing in U.S.D.A. Hardiness Zone Nos. 4 to 8.

Typical *Rhus typhina* plants form dissimilarly colored medium green new foliage that changes to bright medium green during the summer with the leaflets being lance-oblong in configuration with a serrate margin. The mature height and spread of the species commonly is approximately 3.7 to 4.6 meters. This can be compared to a typical mature height and spread for the new cultivar of only approximately 1.8 meters. The leaflet coloration and overall plant size can be used to well differentiate the new cultivar of the present invention. The new cultivar additionally displays a relatively tight growth habit that can be distinguished from the more loose growth habit that commonly is displayed by the species.

The new cultivar of the present invention can be readily distinguished from its parent 'Laciniata' cultivar in view of the atypical coloration of the foliage and the dwarf growth habit. More specifically, the 'Laciniata' cultivar (non-patented in the United States) forms consistently green new foliage, and lacks a dwarf growth habit. The height of the 'Laciniata' cultivar commonly is approximately 2.5 m and the spread commonly is approximately 3 to 4.6 m. The leaflets of the new cultivar are lanceolate in configuration and irregularly incised with deeper incision towards the base while the leaflets of the 'Laciniata' cultivar tend to be more finely incised. Also, the new cultivar is believed to be spread by suckers at a slower rate, and to form more yellow and less orange-red fall foliage coloration.

The 'Dissecta' cultivar (non-patented in the United States) forms dissimilar leaflets that are pinnately dissected producing a finer texture.

The new cultivar of the present invention has been asexually propagated by the rooting of cuttings at St. Paul, Minn., U.S.A. The distinctive characteristics of the new cultivar have been found to be stable and to be capable of transmission from one generation to another following such asexual propagation at St. Paul, Minn.

The new cultivar of the present invention has been named 'Bailtiger', and is being marketed under the TIGER EYES trademark.

BRIEF DESCRIPTION OF THE PHOTOGRAPHS

The accompanying photographs show, as true as reasonably possible to make the same in color illustrations of this character typical plants of the new cultivar. The plants were propagated by the rooting of cuttings and were photographed when approximately two and three years of age while growing outdoors at St. Paul, Minn., U.S.A.

DETAILED DESCRIPTION

Figure 1:
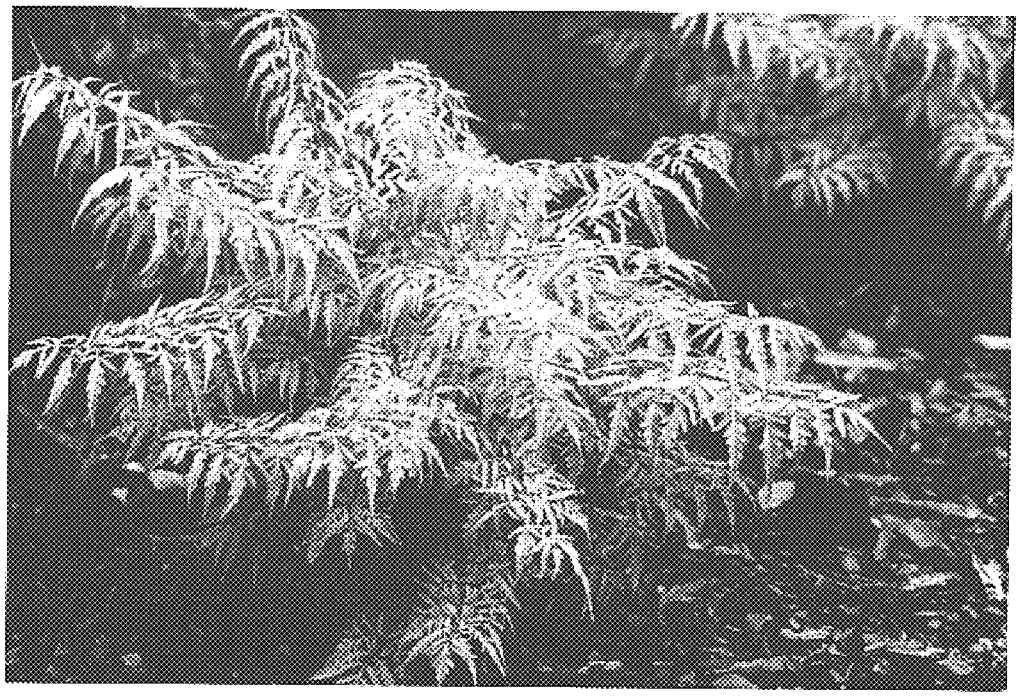
FIG. 1 shows the attractive chartreuse green young foliage.
Figure 2:
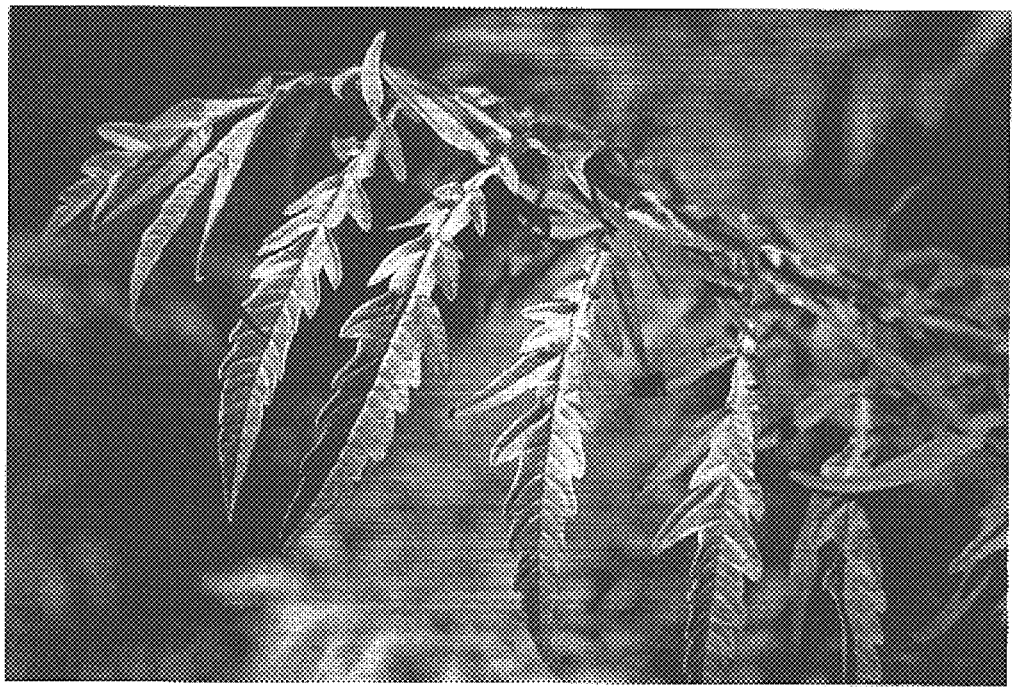
FIG. 2 shows a closer view of the young chartreuse green foliage where more detail can be observed.
Figure 3:
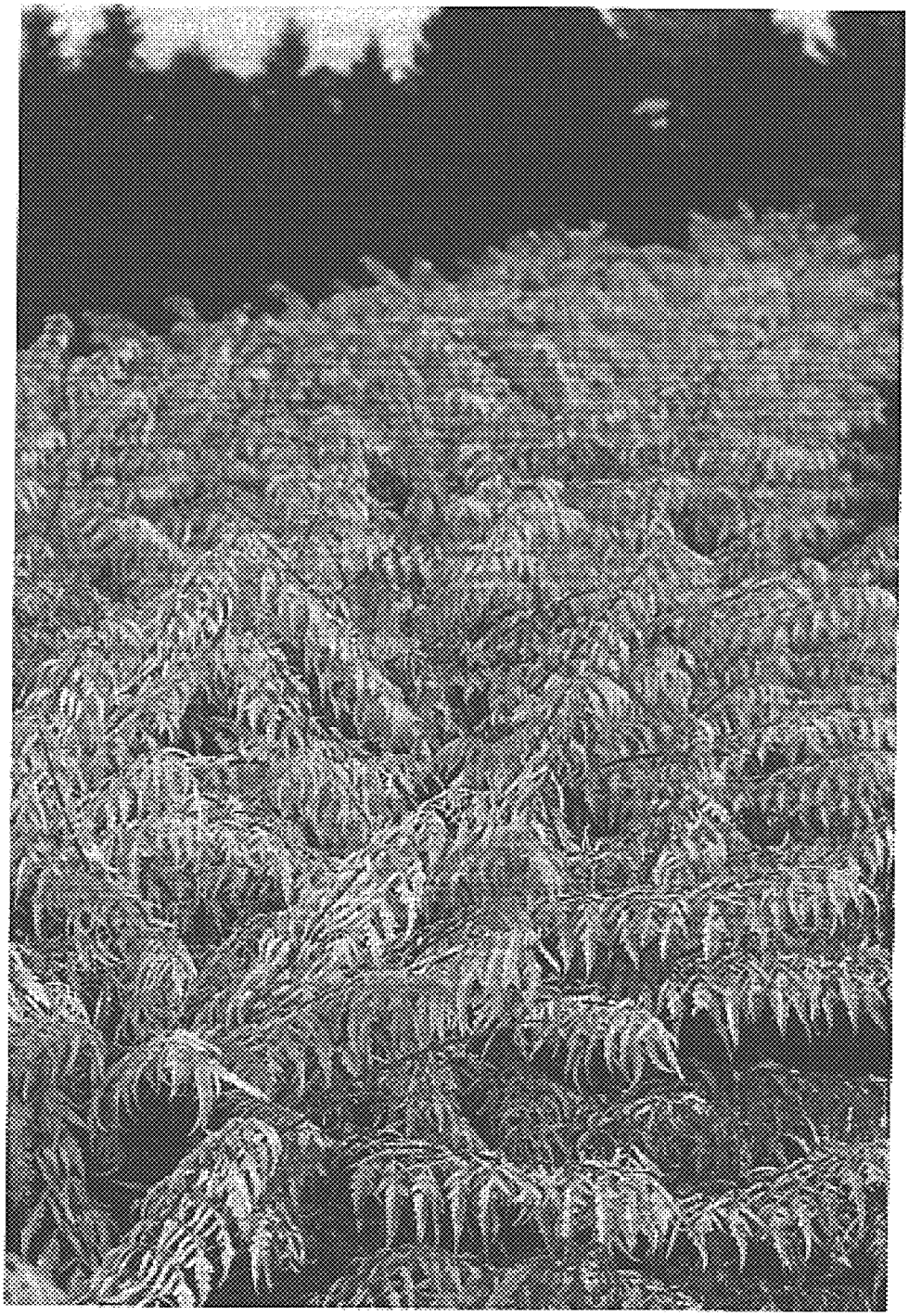
FIG. 3 shows from a distance a mass of the vigorous plant vegetation wherein the foliage has largely assumed more yellow coloration. The purplish coloration of the rachis also is shown.
Figure 4:
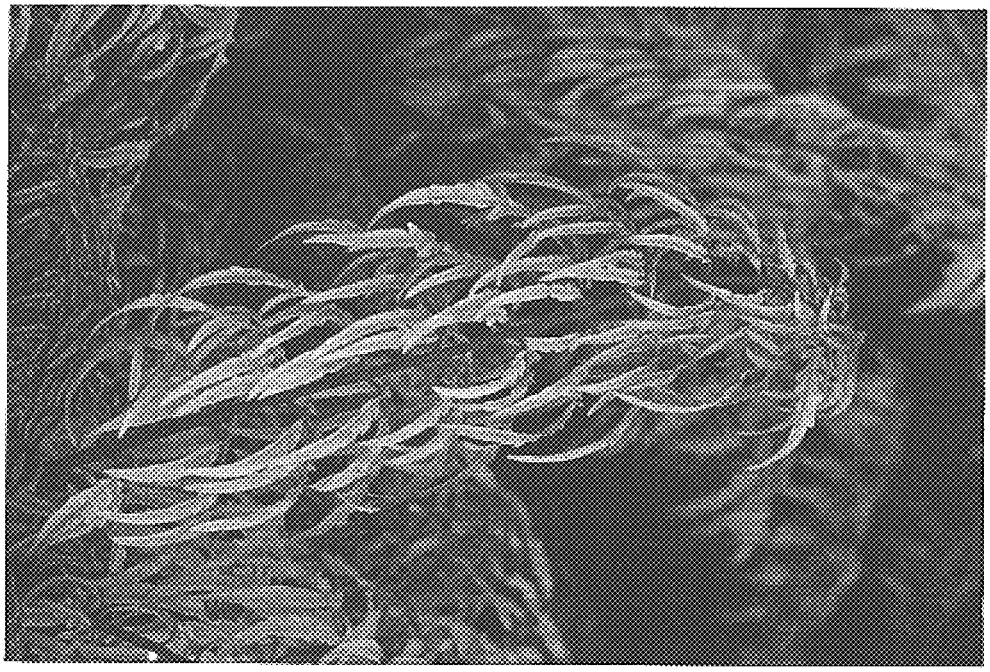
FIG. 4 shows a closer view of the largely yellow foliage and the purplish coloration of the petioles and rachis.
Figure 5:
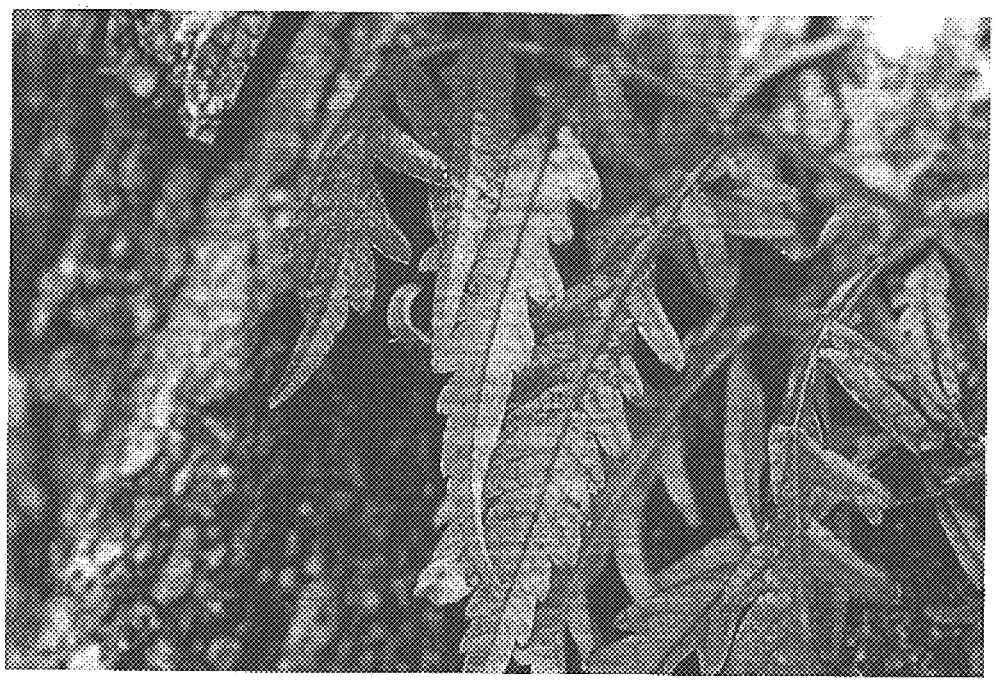
FIG. 5 shows mature leaflets in the fall that are predominantly yellow and include some scarlet coloration.

The chart used in the identification of the colors is The R.H.S. Colour Chart of The Royal Horticultural Society, London, England. Common terms are to be accorded their ordinary dictionary significance. The description is based upon the observation during June and July 2003 of three and four year-old plants propagated by the use of rooted cuttings and growing outdoors at St. Paul, Minn., U.S.A.

Botanical classification: *Rhus typhina*, cv. 'Bailtiger'.

Plant:

*Growth habit.*—Dwarf, compact and spreading with a somewhat flat crown.

*Size.*—Forms a shrub of approximately 1.8 m in height and approximately 1.8 m width. This can be compared to the 'Laciniata' cultivar that commonly reaches a height of approximately 2.7 m with spread of approximately 4 to 5 m.

Branches:

*Stem color.*—Young stems commonly are a blend of Yellow-Green Group 144A and 144B and Grey-Brown Group 199A and 199B.

*Texture.*—Younger stems of approximately one to three years of age commonly are pubescent and the older wood commonly is smooth.

*Leaf scar.*—Black Group 202A in coloration.

*Lenticels.*—Greyed-Green Group 197C in coloration.

*Bark.*—Greyed-Green Group 197A in coloration.

Foliage:

*Leaf shape.*—Lanceolate.

*Arrangement.*—Alternate, and pinnately compound.

*Leaf apex.*—Acute.

*Leaf margins.*—Irregularly incised with deeper incision towards the base.

*Leaf size.*—Commonly approximately 30 to 68 cm in length.

*Leaflet size.*—Commonly approximately 6.5 to 14 cm in length and approximately 1.5 to 3.75 cm in width.

*Rachis texture.*—Pubescent.

*Young foliage.*—Leaflet upper surface: Commonly between Yellow-Green Group 144B and 144C with highlights of Yellow-Green Group 145C, and Greyed-Purple Group 187C on the margin primarily when shaded by other leaves. Leaflet under surface: Commonly between Yellow-Green Group 145A and 145B. Petiole upper surface: Pubescent and Yellow-Green Group 145A with highlights of Greyed-Red Group 179A. Petiole under surface: Pubescent and Yellow-Green Group 145B. Rachis upper surface: Pubescent and commonly Yellow-Green Group 145A with highlights of Greyed-Red Group 179A. Rachis under surface: Yellow-Green Group 145B.

*Adult foliage in full sun.*—Leaflet upper surface: Yellow Group 7A suffused with Yellow-Green Group 144B and Yellow-Green Group 145A. Leaflet under surface: Yellow-Green Group 145B and 145C suffused with Yellow Group 10A. Petiole upper surface: Pubescent and Greyed-Purple Group 187C. Petiole under surface: Pubescent and Yellow-Green Group 145B. Rachis upper surface: Pubescent and Greyed-Purple Group 187C. Rachis under surface: Pubescent and Yellow-Green Group 145B.

*Adult foliage at inner location.*—Leaflet upper surface: Yellow-Green Group 144A with some lower leaflets being suffused with Yellow Group 8A and Greyed-Red Group 179A and 179B and Greyed-Red Group 181A. Leaflet under surface: Commonly between Yellow-Green Group 144C and 144D. Petiole upper surface: Pubescent and Greyed-Purple Group 187B. Petiole under surface: Pubescent and Yellow-Green Group 145B. Rachis upper surface: Pubescent and Greyed-Purple Group 187B. Rachis under surface: Pubescent and Yellow-Green Group 145B.

*Fall foliage.*—Leaflet upper surface: Commonly predominantly yellow, between Yellow Group 12A and 12B, suffused with Yellow-Green Group 144A and 144B and some Greyed-Red Group 181A and 181B and Greyed-Red Group 184A. This can be compared to the more orange-red fall coloration of the 'Laciniata' cultivar. Leaflet under surface: Greyed-Yellow Group 160A suffused with Yellow Group 11B and some Red Group 43A and 43B. Petiole upper surface: Pubescent and Greyed-Purple Group 184A and Red Group 46A. Petiole under surface: Pubescent and Yellow-Green Group 145B. Rachis upper surface: Pubescent and Greyed-Purple Group 184A and Red Group 46A. Rachis under surface: Pubescent and Yellow-Green Group 145B.

Inflorescence: The plants have not flowered during the 2002 and 2003 growing seasons. Accordingly, no seed set has been available for evaluation during observations to date.

Hardiness: Can be grown in U.S.D.A. Hardiness Zone Nos. 4 to 8.

Culture: Performs best in a sunny setting and once established is relatively drought tolerant.

Disease/pest resistance: Has proven to be relatively free of disease and insect problems during observations to date.

Landscape usage: Provides a hardy highly ornamental shrub that imparts coloration to the landscape. The plant can be grown as a specimen shrub or as a mass planting. It further can be grown behind a shrub or perennial border to supply contrasting texture and coloration.

I claim:

1. A new and distinct Staghorn Sumac plant having the following combination of characteristics:

(a) exhibits a dwarf growth habit, (b) forms attractive chartreuse green new foliage that quickly largely changes to bright yellow, and in the fall displays predominantly yellow foliage with some scarlet coloration, (c) is relatively free of insect and disease problems, and (d) is well-suited for growing as a distinctive ornamental shrub in the landscape;

substantially as illustrated and described.

* * * * *